(12) United States Patent
Trapp

(10) Patent No.: US 7,305,897 B2
(45) Date of Patent: Dec. 11, 2007

(54) SAMPLE MACHINING DEVICE AND SAMPLE ANALYSIS DEVICE

(75) Inventor: Monika Trapp, Gevelsberg (DE)

(73) Assignee: Pfaff AQS GmbH automatische Qualitatskontrollsysteme (DE)

( * ) Notice: Subject to any disclaimer, the term of this patent is extended or adjusted under 35 U.S.C. 154(b) by 106 days.

(21) Appl. No.: 11/058,543

(22) Filed: Feb. 15, 2005

(65) Prior Publication Data

US 2006/0070465 A1    Apr. 6, 2006

(30) Foreign Application Priority Data

Oct. 4, 2004    (DE) ................. 20 2004 015 484 U

(51) Int. Cl.
*G01N 1/04* (2006.01)
*G01N 1/38* (2006.01)
(52) U.S. Cl. ................................ 73/864.41; 73/864.81
(58) Field of Classification Search ............. 73/864.41, 73/864.81, 863; 83/919; 356/36; 422/78
See application file for complete search history.

(56) References Cited

U.S. PATENT DOCUMENTS

| | | | | |
|---|---|---|---|---|
| 2,276,757 A | * | 3/1942 | Baines ........................ | 409/184 |
| 4,322,189 A | | 3/1982 | Briese ........................ | 409/136 |
| 4,773,799 A | * | 9/1988 | Guironnet ............ | 73/864.41 X |
| 4,833,930 A | * | 5/1989 | Okamoto et al. ......... | 83/919 X |
| 5,228,177 A | * | 7/1993 | Herzog et al. ............... | 29/33 R |
| 5,678,466 A | * | 10/1997 | Wahl ........................... | 83/168 |

FOREIGN PATENT DOCUMENTS

| | | |
|---|---|---|
| DE | 3344944 C3 | 8/1991 |
| DE | 43 09 134 A1 | 9/1994 |
| DE | 298 06 237 U1 | 7/1998 |
| DE | 44 13 090 C2 | 8/1999 |
| DE | 198 05 394 A1 | 8/1999 |
| DE | 199 12 942 A1 | 10/1999 |
| DE | 299 23 909 U1 | 8/2001 |
| DE | 101 60 219 A1 | 6/2003 |
| DE | 102 51 922 A1 | 6/2003 |
| DE | 102 20 054 B4 | 11/2003 |
| EP | 0 470 961 B1 | 2/1992 |
| WO | WO 91/14166 | 9/1991 |

\* cited by examiner

*Primary Examiner*—Thomas P. Noland
(74) *Attorney, Agent, or Firm*—St. Onge Steward Johnston & Reens LLC

(57) ABSTRACT

The invention relates to a sample machining device, in particular for preparing samples for OES and/or XRF and/or combustion analyses, having at least one sample holder, and to provide a development which is advantageous in use proposes that the machining device includes a cylindrical milling cutter, the cylindrical milling cutter and the sample holder being movable relative to one another in such a manner that a sample which can be held in the sample holder can be divided by means of the cylindrical milling cutter to produce a free piece and a remainder piece of the sample which can still be held in the sample holder, and that at least one additional tool, in particular a drilling or separate milling tool, is provided in order to produce chips from the remainder piece of the sample. Moreover, the invention relates to a sample analysis device in which, according to the invention, the abovementioned sample machining device and means for carrying out OES analysis and/or XRF analysis and/or combustion analysis are provided.

19 Claims, 1 Drawing Sheet

SAMPLE MACHINING DEVICE AND SAMPLE ANALYSIS DEVICE

CROSS-REFERENCE TO RELATED APPLICATIONS

This application claims priority of pending German Patent Application No. 20 2004 015 484.6 filed on Oct. 4, 2004.

FIELD OF THE INVENTION

The invention relates to a sample machining device, in particular for preparing samples for OES and/or XRF and/or combustion analyses, having at least one sample holder.

SUMMARY OF THE INVENTION

Sample machining devices of the type mentioned in the introduction are known. They have a cutting disk. In this way, a sample which has been inserted into the sample holder and is, for example, in the shape of a cone is divided at 90 degrees to the longitudinal axis approx. 20 to 25 mm below the smaller end face. With regard to further sample preparation, it is known to grind the upper part of the sample on a grinding machine for a subsequent possible OES analysis, while a disk, for example with a thickness of approx. 4 mm is cut from the lower part of the sample. This disk is placed into a stamp and in this way sample pieces with a diameter of likewise 4 mm are stamped out of the disk. The stamped pieces are then pneumatically transported to combustion analyzers for detecting carbon (C), sulfur (S), nitrogen (N) and oxygen (O). Therefore, to prepare the samples for subsequent analyses, the known sample machining device requires additional means and a series of further working steps. An additional factor is that in particular in this context there is a risk of the fresh, i.e. particularly pure, metal surface required for the analyses being contaminated by constituents of the air, thereby reducing their suitability for the investigations.

Proceeding from this, the invention is based on the object of developing a sample machining device of the type mentioned in the introduction in a manner advantageous for use such that the abovementioned drawbacks are as far as possible avoided.

DETAILED DESCRIPTION OF THE INVENTION

Figure 1:
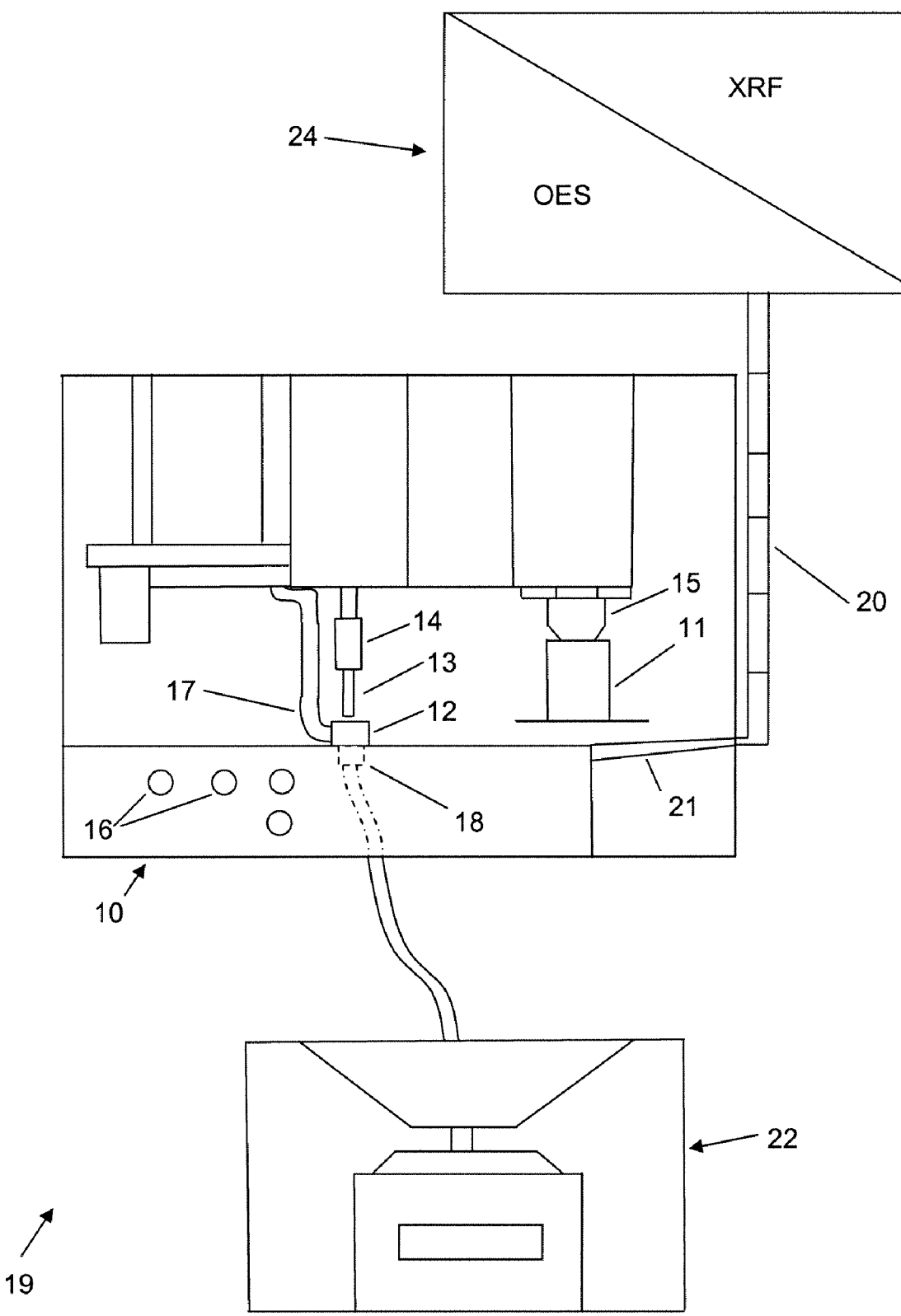
FIG. 1 is a schematic view of a sample machining device according to the present invention.

According to the invention, this object is achieved first and foremost by virtue of the fact that the sample machining device 10 includes a cylindrical milling cutter 11, the cylindrical milling cutter 11 and the sample holder 12 being movable relative to one another in such a manner that a sample which can be held in the sample holder 12 can be divided, in the state held therein, by means of the cylindrical milling cutter 11 to produce a free piece of the sample and a remainder piece of the sample which can still be held in the sample holder 12, and that at least one additional tool 13, in particular a drilling or separate milling tool, is provided in order to produce chips from the remainder piece of the sample. Suitable samples are preferably metal samples, for example cast samples and the like. The cylindrical milling cutter 11 is such that it is suitable for dividing the sample and achieving clean machined surfaces on the pieces formed in the same operation. A sample machining device of this type advantageously on the one hand ensures that the cutting of the sample into pieces, at a freely removable piece which is thereby formed, leads directly, i.e. immediately, to a clean machined surface which is suitable for subsequent investigations, in particular OES and/or XRF investigations, so that there is no need for any subsequent remachining, such as for example grinding.

The invention also achieves improvements with regard to the preparation of the sample remainder piece. The latter, after the dividing operation by means of the cylindrical milling cutter 11, such that it likewise has a correspondingly clean machined surface as a result of the milling operation, can directly remain in the sample holder 12 and can then be machined further therein. According to the invention, an additional tool 13, in particular a drilling or separate milling tool, is for this purpose used to produce chips from the remainder piece of the sample, which chips are suitable, for example, for carrying out combustion analyses. Compared to the abovementioned prior art, the sample machining device 10 according to the invention achieves time-saving machining of the samples and in particular allows a high quality of preparation for OES and/or XRF and/or combustion analyses. In this context, the abbreviation OES, which is known per se, stands for optical emission spectrometry (optical emission spectroscopy) and the abbreviation XRF stands for X-ray fluorescent spectrometry (X-ray fluorescence spectroscopy).

It is preferably provided that the sample holder 12 can be displaced in the lateral and/or vertical direction at least between machining positions of the cylindrical milling cutter 11 and of the additional tool 13. As an alternative or in combination with this measure, it is possible for the cylindrical milling cutter 11 and/or the additional tool 13 to be displaceable in the lateral and/or vertical direction for the purpose of a corresponding position change and/or to carry out the associated machining. A simple structure is made possible by the cylindrical milling cutter 11 being disposed on a first spindle 14 and the additional tool 13 being disposed on a second spindle 15. Furthermore, it is preferred if the sample holder 12 is adapted to holding rotationally symmetrical samples, the sample center line extending at least substantially parallel to the rotation center line of the cylindrical milling cutter 11. The result of this is that the parting plane of the workpiece defined by the cylindrical milling cutter 11 extends at an angle of 90 degrees to the sample longitudinal axis, i.e. perpendicular to the sample longitudinal axis. A refinement according to which the sample holder is adapted to holding conical samples, so that the wider foot end of the sample is received in the sample holder and the narrowing sample section protrudes from the sample holder, is also preferred. Alternatively, it is possible for the sample holder to be adapted to the reverse form of fixing of the sample, i.e. with the widening section protruding. Conical samples have the advantage over cylindrical samples of being easier to demold during production in the casting process.

With regard to possible adapting to conical samples, it is also preferred if the sample machining device 10 is adapted to receiving conical samples, the larger end diameter of which is in the range from 36 to 45 mm and/or the smaller end diameter of which is in the range from 28 to 36 mm and/or the height of which is in the range from 45 to 65 mm.

According to a further aspect, it is possible to provide control means 16 for the in particular automatic centering of the additional tool 13 with respect to the clamping region of the sample holder 12. In this case, the control means 16 may suitably be adapted for in particular automatic alignment of the additional tool 13 to the remainder piece of the sample in order to form chips from a central region of the sample, in particular from the center of its surface formed by the cylindrical milling cutter 11. This makes it possible to remove chips which are unaffected by sample boundary influences from the interior of the sample, for example in order for combustion analyses to be carried out. It is also possible for the milling cutter or drill provided as the additional tool 13 to be specifically adapted to forming and removal of chips from the surface of the remainder piece.

According to a further aspect of the invention, it is possible for the sample machining device to have a purge device 17 for supplying inert gas, in particular argon (Ar), helium (He), nitrogen ($N_2$) or the like, to at least one milling and/or drilling region of the sample machining device. This makes it possible to purge the machining regions of cylindrical milling cutter and/or additional tool with inert gas flowing over them, so that contamination by air elements is avoided at the metallically pure surfaces formed on the sample or sample parts, with the result that better conditions are obtained for subsequent analyses. As an alternative to or in combination with this measure, it is possible for an extraction device 18 for sucking out chips that are to be produced by means of the additional tool 13 to be provided at the sample machining device 10. An extraction device 18 of this type provides the advantage that on the one hand continuous removal of chips and therefore uniform machining conditions are obtained and, moreover, short transport times are possible for the chips, for example to an analysis device 22, such as a combustion analyzer or the like. An expedient refinement is considered to reside in the extraction device having at least one transport fan which sucks the inert gas out of the at least one milling and/or drilling region as carrier gas for the chips in the extraction device. The result of this is that the inert gas even during transport still maintains protection for the chips against contamination from constituents of the air, so that the chips can be fed to an analysis device with a high level of purity.

Moreover, the invention relates to a sample analysis device 19 which has at least one sample machining device 10 according to one or more of the features explained above and at which sample analysis device means 24 for carrying out OES analysis and/or XRF analysis and/or combustion analysis are provided. For analyses to be carried out, a sample analysis device 19 of this type allows prior, preparatory machining of samples and then immediately afterwards allows the analysis (analyses) itself/themselves to be carried out on freshly machined sample material of a high quality. Spectrometers or spectroscopes which are known per se are suitable for the OES and/or XRF analysis. The sample analysis device 19 may have conveying means 20 which are adapted to transporting the free piece of the sample which has been cut off by the cylindrical milling cutter 11 to the said means in order for the OES and/or XRF analysis to be carried out. The transport means 20 of this type used may, for example, be conveyor belts, a tube post system or similar application. In addition, it is possible to provide automated handling means 21, for example for loading the conveying means 20 and/or introducing the piece which has been cut off into the spectrometer or spectroscope.

As an alternative or in combination, the sample analysis device 19 may have a number of thermal analyzers 22, which are preferably adapted for detecting carbon (C), sulfur (S), nitrogen (N) and/or oxygen (O). In the sample analysis device 19 according to the invention, these analyzers 22 can preferably be used to examine the chips produced from the remainder piece of the sample by means of the additional tool 13 of the sample machining device 10. To continuously and quickly transport the chips from the sample machining device 10 to the thermal analyzers 22, the sample analysis device 19 may have means 18 for pneumatically transporting chips. In this context, in particular the extraction device 18 may be adapted for transporting chips and inert gas as carrier gas for the chips from the sample machining device 10 to the thermal analyzers 22. The chips and the inert gas may, for example, be transported from the sample machining device 10 to the analyzers 22 in a pipeline under the influence of a pressure drop effected by the transport fan.

A method for using the sample machining device 10 according to the invention which is included by the invention is as follows: a for example conical sample, preferably a metal sample, more preferably a cast sample, is placed into a sample holder 12 of the sample machining device 10 and divided using the cylindrical milling cutter 11 of this device. The upper piece, i.e. the piece remote from the sample holder, of the sample is finished, i.e. it already has the surface which it requires for a subsequent possible OES and/or XRF analysis. The lower part of the sample is still located in the sample holder 12 of the sample machining device 10. The sample holder 12 with this remainder piece of the sample held in it, is moved to beneath an additional tool 13, preferably a drill or a special milling head, which is preferably secured to a second spindle 15. The additional tool 13 drills out or removes chips from the sample body held in the sample holder 12, preferably from the center of the sample body. In a preferred realization of the method, the chips are sucked out by means of an extraction device 18 and are preferably transported onwards pneumatically. According to a likewise preferred refinement of the method, at least one drilling and/or milling region of the sample machining device is purged with inert gas flowing over it, so that contamination of sample material by air elements is avoided. The method for using the sample machining device 10 or sample analysis device 19 according to the invention is preferably carried out in such a manner that the free piece which has been cut off the sample by means of the cylindrical milling cutter 11, after it has been cut off, is transported directly to analysis devices 24 which are preferably suitable for carrying out OES and/or XRF analysis. With regard to the chips produced by the additional tool 13 it is preferred for these chips to be transported pneumatically to thermal analyzers 22. The extraction device 18 can expediently be used for this purpose. This extraction device 18 can suck out the inert gas which has been purged onto the at least one milling and/or drilling region by means of a transport fan, and this inert gas can then be used as carrier gas for passing the chips to the thermal analyzers 22.

All features disclosed are (inherently) pertinent to the invention. The disclosure content of the associated/appended priority documents (copy of the prior application) is hereby incorporated in its entirety in the disclosure of the application, partly with a view to incorporating features of these documents in claims of the present application.

What is claimed is:

1. Sample machining device having at least one sample holder, characterized in that the machining device includes a cylindrical milling cutter, the cylindrical milling cutter and the sample holder being movable relative to one another in such a manner that a sample which can be held in the sample holder can be divided by means of the cylindrical milling cutter to produce a free piece and a remainder piece of the sample which can still be held in the sample holder, and in that at least one additional tool is provided in order to produce chips from the remainder piece of the sample.

2. Sample machining device according to claim 1, characterized in that the sample holder can be displaced in the lateral and/or vertical direction at least between machining positions of the cylindrical milling cutter and of the additional tool.

3. Sample machining device according to claim 1, characterized in that the cylindrical milling cutter is disposed on a first spindle and the additional tool is disposed on a second spindle.

4. Sample machining device according to claim 1, characterized in that the sample holder is adapted to holding rotationally symmetrical samples, so that a sample center line extends at least substantially parallel to the rotation center line of the cylindrical milling cutter.

5. Sample machining device according to claim 1, characterized in that the sample holder is adapted to holding conical samples, so that a wider foot end of the sample is received in the sample holder and a narrowing sample section protrudes from the sample holder.

6. Sample machining device according to claim 1, characterized in that the sample machining device is adapted to receiving conical samples, a larger end diameter of which is in the range from 36 to 45 millimeters and/or a smaller end diameter of which is in the range from 28 to 36 millimeters and/or the height of which is in the range from 45 to 65 millimeters.

7. Sample machining device according to claim 1, characterized in that control means are provided for the automatic centering of the additional tool with respect to a clamping region of the sample holder.

8. Sample machining device according to claim 1, characterized in that a control means are adapted for automatic alignment of the additional tool to the remainder piece in order to form chips from a central region, in particular from the center of a surface thereof formed by the cylindrical milling cutter.

9. Sample machining device according to claim 1, characterized in that the at least one additional tool is adapted for removal of chips from a surface of the remainder piece.

10. Sample machining device according to claim 1, characterized in that a purge device for supplying inert gas into at least one milling and/or drilling region of the sample machining device is provided.

11. Sample analysis device according to claim 10, characterized in that the inert gas comprises at least one of argon, helium and nitrogen.

12. Sample machining device according to claim 1, characterized in that an extraction device for sucking out chips that are to be produced by means of the additional tool is provided.

13. Sample machining device according to claim 12, characterized in that the extraction device has at least one transport fan which sucks the inert gas out of at least one milling and/or drilling region as carrier gas for the chips.

14. Sample analysis device, characterized in that at least one sample machining device according to claim 1 is provided, and in that means for carrying out OES analysis and/or XRF analysis and/or combustion analysis are provided.

15. Sample analysis device according to claim 14, characterized in that conveying means are provided for transporting the free piece of the sample from the sample machining device to means for carrying out OES analysis and/or XRF analysis.

16. Sample analysis device according to claim 15, characterized in that a number of thermal analyzers are provided, adapted for detecting carbon, sulfur, nitrogen and oxygen.

17. Sample analysis device according to claim 16, characterized in that means for pneumatically transporting chips from the sample machining device to the thermal analyzers are provided.

18. Sample analysis device according to claim 17, characterized in that the extraction device is adapted for transporting chips and inert gas as carrier gas from the sample machining device to the thermal analyzers.

19. Sample analysis device according to claim 1, characterized in that the at least one additional tool comprises a drilling or separate milling tool.

* * * * *